US006790619B2

(12) United States Patent
Meissner et al.

(10) Patent No.: US 6,790,619 B2
(45) Date of Patent: Sep. 14, 2004

(54) PLANT PHOSPHOMEVALONATE KINASES

(75) Inventors: Ruth Meissner, Leverkusen (DE); Christa Lechelt-Kunze, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/988,863

(22) Filed: Nov. 21, 2001

(65) Prior Publication Data

US 2002/0123427 A1 Sep. 5, 2002

(30) Foreign Application Priority Data

Nov. 22, 2000 (DE) .......................................... 100 57 755

(51) Int. Cl.$^7$ ............................ C12Q 1/68; C12N 9/00; C12N 9/99; C07K 17/00; A01H 11/00
(52) U.S. Cl. ......................... 435/6; 435/183; 435/184; 530/350; 800/295; 800/300
(58) Field of Search ........................... 435/6, 183, 184; 530/350; 800/295, 300

(56) References Cited

FOREIGN PATENT DOCUMENTS

| WO | 00/15809 | 3/2000 | ........... C12N/15/82 |
|---|---|---|---|
| WO | 00/36081 | 6/2000 | |
| WO | 00/53782 | 9/2000 | ........... C12N/15/82 |
| WO | 01/14533 | * 3/2001 | ............ C12N/9/00 |

OTHER PUBLICATIONS

Lange et al. Proc. Natl. Aca. Sci. U.S.A., 1999, vol. 96(24), p. 13714–13719.*

Nucleic Acids Res., vol. 25, No. 17, (month unavailable) 1997, pp. 3389–3402, Stephen F. Altschul, Thomas L. Madden, Alejandro A. Schäffer, Jinghui Zhang, Zheng Zhang, Webb Miller and David J. Lipman, "Gapped BLAST and PSI–BLAST: a new generation of protein database search programs."

Nucleic Acids Research, vol. 12(22), (month unavailable) 1984, pp. 8711–8721, Michael Bevan, "Binary Agrobacterium vectors for plant transformation."

Plant Physiol., 98, (month unavailable), 1992, pp. 1515–1517, Rodney Croteau, "Clomazone Does Not Inhibit the Conversion of Isopentenyl Pyrophosphate to Geranyl, Farnesyl, or Geranylgeranyl Pyrophosphate in Vitro."

Proc. Natl. Acad. Sci., vol. 93, pp. 6025–6030, Jun. 1996, Luda Diatchenko, Yun–Fai Chris Lau, Aaron P. Campbell, Alex Chenchik, Fauzia Mooadam, Betty Huang, Sergey Lukyanov, Konstantin Lukyanov, Nadya Gurskaya, Eugene D. Sverdlov and Paul D. Siebert, "Suppression subtractive hybridization: A method for generating differentially regulated or tissue–specific cDNA probes and libraries".

Plant Physiol (month unavailable) 1990, 93, pp. 1121–1127, Adolf Heintze, Jörn Görlach, Carola Leuschner, Petra Hoppe, Petra Hagelstein, Detlef Schulze–Siebert and Gernot Schultz, "Plastidic Isoprenoid Synthesis during Chloroplast Development".

The Plant Journal, (month unavailable) 1992, 2(3) pp. 417–422, Michèle Minet, Marie–Elisabeth Dufour and Francois Lacroute, Complementation of *Saccharomyces cerevisiae* auxotrophic mutants by *Arabidopsis thaliana* cDNAs.

Annu. Rev. Plant Mol. Biol. 40, (month unavailable) 1989, pp. 39–59, H. Kleinig, "The Role of Plastids in Isoprenoid Biosynthesis".

Gene, 156 (month unavailable) 1995, pp. 119–122, Dominik Mumberg, Rolf Müller and Martin Funk, "Yeast vectors for the controlled expression of heterologous proteins in different genetic backgrounds".

Plant Physiol. 94, Jun. 1990, pp. 704–709, Michael A. Norman, Rex A Liebl and Jack M. Widholm, Site of Clomazone Action in Tolerant–Soybean and Susceptible–Cotton Photomixotrophic Cell Suspension Cultures.

Plant Physiol. 98, (month unavailable) 1992, pp. 427–432, Monte R. Weimer, Nelson E. Balke and Douglas D. Buhler, "Herbicide Clomazone Does Not Inhibit In Vitro Geranylgeranyl Synthesis from Mevalonate".

Database EMBL 'Online! Accession No. AAB18130, Nov. 8, 2000, XP002191330.

Database EMBL 'Online! Accession No. AA660847, Nov. 14, 1997, XP002191331.

Database EMBL 'Online! Accession No. BF070746, Oct. 18, 2000, XP002191332.

Database EMBL 'Online! Accession No. AC079041, Aug. 18, 2000, XP002191333.

Database EMBL 'Online! Accession No. Q9C6T1, Jun. 1, 2001, XP002191334.

Database EMBL 'Online! Accession No. AF429385, Oct. 27, 2001, XP002191335.

Molecular and Cellular Biology, American Society for Microbiology, Washington, US, Bd. 11, Nr. 2, Feb. 1991, Seiten 620–631, XP000981936, ISSN: 0270–7306, Seiten 620, 626:Absatz 2, Abbildungen 4,5, Y. H. Tsay et al, "Cloning and Characterization of ERG8, an Essential Gene of *Saccharomyces cerevisiae* that Encodes Phosphomevalonate Kinase".

(List continued on next page.)

*Primary Examiner*—Kenneth R. Horlick
*Assistant Examiner*—Joyce Tung
(74) *Attorney, Agent, or Firm*—Richard E. L. Henderson; Raymond J. Harmuth

(57) ABSTRACT

The invention relates to nucleic acids which encode plant polypeptides with the biological activity of phosphomevalonate kinases, to the polypeptides encoded by them and their use as targets for herbicides and their use for identifying novel, herbicidally active compounds, and to methods for finding modulators of these polypeptides.

4 Claims, 1 Drawing Sheet

OTHER PUBLICATIONS

Molecular Genetics and Metabolism, Bd. 72, Nr. 3, Mar. 2001, Seiten 273–276, XP001038655, ISSN: 1096–7192, S. M. Houten et al, "Nonorthologous Gene Displacement of Phosphomevalonate Kinase".

Progress in Lipid Research, Pergamon Press, Paris, FR, Bd. 36, Nr. 2/3, Sep. 1997, Seiten 197–226, XP000957903, ISSN: 0163–7827, Seiten 197, 199, 204, T. J. Bach et al, "Cloning of CDNAS or Genes Encoding Enzymes of Sterol Biosynthesis from Plants and Other Eukaryotes: Heterologous Expression and Complementation Analysis of Mutations for Functional Characterization".

Database EMBL Online!, Accession No. Q9UT88, May 1, 2000, XP002191336.

Plant Physiology (Bethesda), Bd. 94, Nr. 2, (month unavailable) 1990, Seiten 704–709, XP001042396, ISSN: 0032–0889, Abstrakt, Seite 708, Tabelle 1,2. M. A. Norman et al, "Site of Clomazone Action in Tolerant Soybean and Susceptible Cotton Photomixotrophic Cell Suspension Cultures".

Phytochemistry, Pergamon Press, GB, Bd. 52, Nr. 6, Nov. 1999, Seiten 975–983, XP004291102, ISSN: 0031–9422, A. E. Schulte et al, "Purification and Characterization of Phosphomevalonate Kinase from Catharanthus Roseus", Zusammenfassung, Seiten 976, 982.

* cited by examiner

Fig. 1

```
A. t.   6 SAPGKVLMTGGYLVLEKPNAGLVLSTNARFYAIVKPINEEVKPESWAWKW  55
          |||||  |: ||||||:         |.  .||  :|:  |         :  .
S. c.   8 SAPGKALLAGGYLVLDTKYEAFVVGLSARMHAVAHPYGSLQGSDKF....  53

56 TDVKLTSPQL.SRESMYKLSLNHLTLQSVSASDSRNPFVEHAIQYAIAAA 104
          :|:. | |    |:|  :|     :  ||    |:|||:|  |   | .
       54 .EVRVKSKQFKDGEWLYHISPKSGFI.PVSIGGSKNPFIEKVI...ANVFS  99

105 HLATEKDKESLHKLLLQGLDITILGSNDFYSYRNQIESAGLPLTPESLGT 154
           :   |       |  .:||    |.|  .|.|  :|        ||  |
      100 YFKPNMDDYCNRNLFV..IDIF...SDD...AYHSQEDS.....VTEHRG. 136

155 LAPFASITFNAAESNGANSKPEVAKTGLGSSAAMTTAVVAALLHYLGVVD 204
             |    |    ..   || |||||||| : |.    ||     :  ||
      137 .........NRRLSFHSHRIEEVPKTGLGSSAGLVTVLTTALASFF.VSD 176

205 LSDPCKEGKFGCSDLDVIHMIAQTSHCLAQGKVGSGFDVSCAVYGSQRYV 254
          | .   .  :       :|||  :||  .||  ||||:||||||. | ||| ||
      177 LENNVDKYR......EVIHNLAQVAHCQAQGKIGSGFDVAAARYGSIRYR 220

255 RFSPEVLSFAQVAVTGLPLNEVIGTILKGKWDNKRTEFSLPPLMNLFLGE 304
          ||  | .:|       .    ...   :   |.       || : |.:|:
      221 RFPPALISNLPDIGSATYGSKLAHLVDEEDWNITIKSNHLPSGLTLWMGD 270

305 PGSGGSSTPSMVGAVKKWQMSDPEKARENWQNLSDANLELETKLNDLSKL 354
          ||   |  :|  ||| |   ...:  |  ||         |. | :|
      271 I.KNGSETVKLVQKVKNWYDSHMPESLKIYTELDHANSRFMDGLSKLDRL 319

355 AKDHWDVYLRVIKSC..SVLTSEKWVLHATEPINEAIIKELLEAREAMLR 402
           .||   .: .|   . |:|:                 |: | |:|.
      320 HETHDDYSDQIFESLERNDCTCQKY.............PEITEVRDAVAT 356

403 IRILMRQMGEAASVPIEPESQTQLLDSTMSAEGVLLAGVPGAGGFDAIFA 452
          ||   |... .   |||  || |||    ..|||   :|||||:|||
      357 IRRSFRKITKESGADIEPPVQTSLLDDCQTLKGVLTCLIPGAGGYDAIAV 406

453 ITLGD 457
          ||  |
      407 ITKQD 411
```

PLANT PHOSPHOMEVALONATE KINASES

TECHNICAL FIELD OF THE INVENTION

The invention relates to nucleic acids which encode plant polypeptides with the biological activity of phosphomevalonate kinases, to the polypeptides encoded by them and their use as targets for herbicides and their use for identifying novel, herbicidally active compounds, and to methods for finding modulators of these polypeptides.

BACKGROUND OF THE INVENTION

Unwanted plant growth can be prevented by using herbicides. The demands made on herbicides with regard to their efficacy, costs and environmental compatibility have been steadily increasing. There exists therefore a demand for new substances which can be developed into potent new herbicides. In general, it is usual to search for such new lead structures in greenhouse tests. However, such tests are laborious and expensive. Accordingly, the number of substances which can be tested in the greenhouse is limited.

Advantageous targets for herbicides are searched for in essential biosynthetic pathways. Thus, the biosynthesis of isoprenoids in plants leads, inter alia, to the synthesis of carotenoids and of the side chains of plastoquinone and of chlorophyll. These products are essential for the photosynthetic growth of plants. The inhibition of one step in this biosynthetic pathway leads to the termination of a plant's growth. Moreover, plant hormones such as gibberellic acid, abscisic acid and brassinosteroids and membrane components (phytosterols), which are also essential for the plant's growth, are formed from isoprenoids.

Isopentyl diphosphate (IPP) is the branching point from which the widest range of isoprenoids are formed. The production of IPP is therefore a critical point in plant metabolism. In plants, IPP is produced via two different metabolic pathways in different compartments. In the endoplasmic reticulum (ER) and in the cytosol, IPP synthesis proceeds via the classic acetate/mevalonate metabolic pathway as it also proceeds in the animal organism. In contrast, IPP is synthesized in chloroplasts via the alternative glyceraldehyde phosphate/pyruvate metabolic pathway. Both metabolic pathways are essential since various isoprenoid metabolites are formed in the different compartments. Moreover, the degree to which the two metabolic pathways are autonomous or to which an exchange of metabolites takes place between the compartments has not been elucidated as yet (Heintze et al., 1990, Kleinig, 1989). (See References section below for full citation to these and other references referred to herein).

Clomazone is a known herbicidal compound which reduces the carotenoid and chlorophyll content in the leaf. For a long time it has been assumed that clomazone acts via the inhibition of the isoprenoid metabolic pathway. Norman et al. (1990) had demonstrated that the site of action would have to be between mevalonate and geranylgeranyl pyrophosphate. This would establish one of the interposed five enzymes, one of which is phosphomevalonate kinase, as the site of action. Somewhat more recent works by Weimer et al. (1992) and Rodney Croteau (1992) suggest, however, that the site of action of clomazone would be found elsewhere.

SUMMARY OF THE INVENTION

Within the context of the present invention, an *Arabidopsis thaliana* cv. Columbia cDNA has been isolated with homology to phosphomevalonate kinase, hereinbelow abbreviated to PMVK, from *Saccharomyces cerevisiae* (FIG. 1). It was possible to induce this gene in *Arabidopsis thaliana* cv. Columbia by treatment with the herbicide chlorsulfuron (10 g/ha).

The homology between the *Saccharomyces cerevisiae* PMVK (=ERG8) and the cDNA isolated from *A. thaliana* amounts to 44% similarity or 35% identity (see FIG. 1, Bestfit with Wisconsin Package Version 10.1). (ERG8 is the name of the gene encoding phosphomevalonate kinase in yeast (*S cerevisiae*)). This corresponds for example to the homology between the *Saccharomyces cerevisiae* mevalonate kinase and the *Arabidopsis thaliana* mevalonate kinase with a similarity of 45% and an identity of 35%. The function was detected for the *Arabidopsis thaliana* mevalonate kinase by complementation of the corresponding mutant from *Saccharomyces cerevisiae*. Moreover, the cDNA isolated within the context of the present invention shows 69% identity with a partial PMVK sequence from *Pinus radiate* in accordance with SEQ ID NO:5, which is of interest for modifying the isoprenoid content, isoprenoid composition and isoprenoid metabolism of plants (WO 00/36 081). Further partial cDNAs from plants (*Medicago trunculata*, Accession Number AA660847, see SEQ ID NO:3 and *Gossypium hirsutum*, Accession Number Al727861, see SEQ ID NO:4) have been isolated as putative PMVKs. Various Arabidopsis spp. sequences (ESTs and genomic sequences) which correspond to the PMVK sequence isolated herein or to parts thereof can be found in databases from various sequencing projects, however, no information is given on the function or importance of these sequences or sequence fragments.

For the first time, the present invention now provides the complete cDNA sequence of a plant phosphomevalonate kinase and describes its use, or the use of the polypeptides encoded thereby, for identifying new herbicidal active compounds.

Subject-matter of the present invention are therefore nucleic acids which encode complete plant phosphomevalonate kinases, with the exception of the partial nucleic acid sequences from *Medicago trunculata* in accordance with SEQ ID NO:3, *Gossypium hirsutum* in accordance with SEQ ID NO:4 and *Pinus radiata* in accordance with SEQ ID NO:5.

Subject-matter of the present invention are, in particular, nucleic acids which encode the *Arabidopsis thaliana* phosphomevalonate kinase.

Subject-matter of the present invention are very particularly nucleic acids which encode the *Arabidopsis thaliana* phosphomevalonate kinase and are described under SEQ ID NO:1 and/or encode a polypeptide in accordance with SEQ ID NO:2 or fragments thereof.

BRIEF DESCRIPTION OF THE DRAWINGS

FIG. 1 is a determination of the homology between the *A. thaliana* phosphomevalonate kinase according to the invention in accordance with SEQ ID NO:2 and the known *S. cerevisiae* phosphomevalonate kinase (BESTFIT) by means of Bestfit (Wisconsin Package Version 10.1 (GCG)). The similarity is 44% and the identity 35%.

SEQ ID NO:1 Nucleic acid sequence encoding *A. thaliana* phosphomevalonate kinase.

SEQ ID NO:2 Amino acid sequence of the *A. thaliana* phosphomevalonate kinase.

SEQ ID NO:3 Nucleic acid fragment from *Medicago trunculata* (putative PMVK) of Accession Number AA 660847.

SEQ ID NO:4 Nucleic acid fragment from *Gossypium hirsutum* (putative PMVK) of Accession Number Al 727861.

SEQ ID NO:5 Nucleic acid fragment from *Pinus radiata* (encoding PMVK in accordance with WO 00/36081).

DETAILED DESCRIPTION OF THE PREFERRED EMBODIMENTS OF THE INVENTION

The nucleic acids according to the invention are, in particular, single-stranded or double-stranded deoxyribonucleic acids (DNA) or ribonucleic acids (RNA).

Preferred embodiments are fragments of the genomic DNA, which may contain introns, and cDNAs.

The nucleic acids according to the invention are preferably DNA fragments which correspond to the cDNA of Arabidopsis plants.

The nucleic acids according to the invention especially preferably encompass a sequence selected from amongst a) the sequence in accordance with SEQ ID NO:1, b) sequences which encode a polypeptide which encompasses the amino acid sequence in accordance with SEQ ID NO: 2, c) part sequences of the sequences defined under a) or b) which have a length of at least 14 base pairs, d) sequences which hybridize with the sequences defined under a) or b) at a hybridization temperature of 35–52° C., e) sequences which have at least 70% identity, preferably 85% identity, especially preferably 90% identity, very especially preferably 95% identity, with the sequences defined under a), f) sequences which have at least 70% identity, preferably 80% identity, especially preferably 90% identity, very especially preferably 95% identity, with the sequences defined under b), g) sequences which are complementary to the sequences defined under a) or b), and h) sequences which, owing to the degeneracy of the genetic code, encode the same amino acid sequence as the sequences defined under a) to f).

A cDNA molecule with the sequence in accordance with SEQ ID NO:1 constitutes a very especially preferred embodiment of the nucleic acids according to the invention.

The term "complete" phosphomevalonate kinase as used in the present context describes the phosphomevalonate kinase which is encoded by a complete coding region of a transcription unit starting with the ATG start codon and encompassing all information-bearing exon regions of the gene present in the organism of origin and encoding phosphomevalonate kinase, and the signals required for correct termination of transcription.

The term "gene" as used in the present context refers to a section from the genome of a cell which section is responsible for the synthesis of a polypeptide chain.

The term "to hybridize" as used in the present context describes the process in which a single-stranded nucleic acid molecule undergoes base pairing with a complementary strand. In this manner, for example, DNA fragments which encode phosphomevalonate kinases which exhibit the same or similar properties as the kinase with the amino acid sequence in accordance with SEQ ID NO: 2 can be isolated from plants other than Arabidopsis, starting from the sequence information disclosed herein.

The term "cDNA" as used in the present context refers to the single- or double-stranded copy of an RNA molecule and, being a copy of biologically active mRNA, is free from introns, i.e. all coding regions of a gene are present in connected form. Hybridization conditions are calculated by approximation using the following formula:

Melting temperature $Tm = 81.5°\ C. + 16.6 \log [c(Na^+)] + 0.41(\%G+C)) - 500/n$ (Lottspeich and Zorbas, 1998).

In this formula, c is the concentration and n the length of the hybridizing sequence segment in base pairs. For a sequence >100 bp, the term 500/n does not apply. At the highest stringency, washing is effected at a temperature of 5–15° C. below Tm and an ionic strength of 15 mM $Na^+$ (corresponds to 0.1×SSC). If an RNA probe is used for hybridization, the melting point is 10–15° C. higher.

Preferred hybridization conditions are indicated hereinbelow:

Hybridization solution: DIG Easy Hyb (Roche)

Hybridization temperature: 35–52° C., preferably 42° C. (DNA-DNA), or 50° C. (DNA-RNA).

1. Wash step: 2×SSC, twice 5 minutes at room temperature;

2. Wash step: twice 15 minutes in 1×SSC, at 50° C.; preferably 0.5×SSC, at 65° C.; especially preferably 0.2×SSC, at 65° C.

The degree of identity of the nucleic acids is preferably determined with the aid of the program NCBI BLASTN Version 2.0.14. (Altschul et al., 1997).

Subject-matter of the present invention are furthermore DNA constructs which encompass a nucleic acid according to the invention and a homologous or heterologous promoter.

The term "homologous promoter" as used in the present context refers to a promoter which controls the expression of the gene in question in the organism of origin.

The term "heterologous promoter" as used in the present context refers to a promoter which has properties other than the promoter which controls the expression of the gene in question in the organism of origin.

The choice of heterologous promoters depends on whether pro- or eukaryotic cells or cell-free systems are used for expression. Examples of heterologous promoters are the cauliflower mosaic virus 35S promoter for plant cells, the alcohol dehydrogenase promoter for yeast cells, and the T3-, T7- or SP6 promoters for prokaryotic cells or cell-free systems.

Subject-matter of the present invention are furthermore vectors comprising a nucleic acid according to the invention, a regulatory region according to the invention or a DNA construct according to the invention. Vectors which can be used are all the phages, plasmids, phagemids, phasmids, cosmids, YACs, BACs, artificial chromosomes or particles which are suitable for particle bombardment that are used in molecular biology laboratories.

Preferred vectors are pBIN (Bevan, 1984) and its derivatives for plant cells, pFL61 (Minet et al., 1992) or, for example, the p4XXprom. series of vectors (Mumberg et al.) for yeast cells, pSPORT vectors (Life Technologies) for bacterial cells, lambdaZAP (Stratagene) for phages or Gateway vectors (Life Technologies) for various expression systems in bacterial cells or in baculovirus.

Subject-matter of the present invention are also host cells comprising a nucleic acid according to the invention, a DNA construct according to the invention or a vector according to the invention.

The term "host cell" as used in the present context refers to cells which do not naturally comprise the nucleic acids according to the invention.

Suitable host cells are not only prokaryotic cells, preferably *E. coli*, but also eukaryotic cells such as cells of *Saccharomyces cerevisiae, Pichia pastoris,* insects, plants, frog oocytes and mammalian cell lines.

Subject-matter of the present invention are furthermore polypeptides with the biological activity of phosphomevalonate kinases which are encoded by the nucleic acids according to the invention.

The term "polypeptides" as used in the present context relates not only to short amino acid chains which are usually termed peptides, oligopeptides or oligomers, but also to longer amino acid chains which are usually termed proteins. It encompasses amino acid chains which can be modified either by natural processes such as posttranslational processing or by chemical prior-art methods. Such modifications can occur at various positions and repeatedly in a polypeptide, such as, for example, at the peptide backbone, at the amino acid side chain, at the amino and/or at the carboxy terminus. They encompass for example acetylations, acylations, ADP ribosylations, amidations, covalent linkages to flavins, haeme moieties, nucleotides or nucleotide derivatives, lipids or lipid derivatives or phosphatidylinositol, cyclizations, the formation of disulphide bridges, demethylations, the formation of cystine, formylations, gamma-carboxylations, glycosylations, hydroxylations iodinations, methylations, myristoylations, oxidations, proteolytic processings, phosphorylations, selenoylations and tRNA-mediated additions of amino acids.

The polypeptides according to the invention may exist in the form of "mature" proteins or as parts of larger proteins, for example as fusion proteins. They may furthermore have secretion or leader sequences, pro-sequences, sequences which allow simple purification, such as repeated histidine residues, or additional stabilizing amino acids.

The polypeptides according to the invention, in particular the polypeptide in accordance with SEQ ID NO:2, need not constitute complete plant phosphomevalonate kinases, but may also just be fragments of these as long as they retain at least the biological activity of the complete plant phosphomevalonate kinase. Polypeptides which exert the same type of biological activity as a phosphomevalonate kinase with an amino acid sequence in accordance with SEQ ID NO:2 are still considered to be in accordance with the invention. The polypeptides according to the invention in this case need not be able to be derived from Arabidopsis phosphomevalonate kinases. Polypeptides which correspond to phosphomevalonate kinases of, for example, the plants stated hereinbelow, or to fragments thereof, and which are still capable of exerting the biological activity thereof are still considered to be in accordance with the invention: tobacco, maize, wheat, barley, oats, rice, rye, tomatoes, legumes, potato plants, *Lactuca sativa*, other Brassicaceae, woody species, *Physcomitrella patens*.

Compared with the corresponding region of naturally occurring phosphomevalonate kinases, the polypeptides according to the invention may exhibit deletions or amino acid substitutions as long as they still exert at least the biological activity of the complete kinase. Conservative substitutions are preferred. Such conservative substitutions encompass variations, where one amino acid is replaced by another amino acid from among the following group:

1. Small aliphatic residues, nonpolar residues or residues of low polarity: Ala, Ser, Thr, Pro and Gly;
2. Polar, negatively charged residues and their amides: Asp, Asn, Glu and Gln;
3. Polar, positively charged residues: His, Arg and Lys;
4. Large aliphatic nonpolar residues: Met, Leu, Ile, Val und Cys; and
5. Aromatic residues: Phe, Tyr and Trp.

Preferred conservative substitutions can be seen from the following list:

| Original residue | Substitution |
|---|---|
| Ala | Gly, Ser |
| Arg | Lys |

-continued

| Original residue | Substitution |
|---|---|
| Asn | Gln, His |
| Asp | Glu |
| Cys | Ser |
| Gln | Asn |
| Glu | Asp |
| Gly | Ala, Pro |
| His | Asn, Gln |
| Ile | Leu, Val |
| Leu | Ile, Val |
| Lys | Arg, Gln, Glu |
| Met | Leu, Tyr, Ile |
| Phe | Met, Leu, Tyr |
| Ser | Thr |
| Thr | Ser |
| Trp | Tyr |
| Tyr | Trp, Phe |
| Val | Ile, Leu |

Subject-matter of the present invention are thus also polypeptides which exert at least the biochemical reaction of the formation of 5-pyrophosphomevalonate from 5-phosphomevalonate, such as phosphomevalonate kinase, and which encompass an amino acid sequence which exhibits at least 60% identity, preferably 80% identity, especially preferably 90% identity, very especially preferably 97–99% identity, with the sequence in accordance with SEQ ID NO:2 over its entire length.

The degree of identity of the amino acid sequences is preferably determined with the aid of the program BLASTP+BEAUTY Version 2.0.14. (Altschul et al., 1997).

A preferred embodiment of the polypeptides according to the invention is the phosphomevelonate kinase (PMVK) with the amino acid sequence in accordance with SEQ ID NO:2.

The PMVK amino acid sequence has a potential ATP binding site in the region of amino acids 177 to 186, which is typical of kinases.

The term "biological activity of a phosphomevalonate kinase" as used in the present context refers to the ability to convert 5-phosphomevalonate into 5-pyro-phosphomevalonate with consumption of ATP and formation of ADP.

The nucleic acids according to the invention can be prepared in the customary manner. For example, the nucleic acid molecules can be synthesized chemically in their entirety. It is also possible chemically to synthesize short sections of the nucleic acids according to the invention, and such oligonucleotides can be radiolabelled or labelled with a fluorescent dye. The labelled oligonucleotides can also be used for screening cDNA libraries generated starting from plant mRNA. Clones which hybridize with the labelled oligonucleotides are selected for isolating the DNA fragments in question. After characterization of the DNA which has been isolated, the nucleic acids according to the invention are obtained in a simple manner.

Alternatively, the nucleic acids according to the invention can be generated by means of PCR methods using chemically synthesized oligonucleotides.

The term "oligonucleotide(s)" as used in the present context denotes DNA molecules composed of 10 to 50 nucleotides, preferably 15 to 30 nucleotides. They are synthesized chemically and can be used as probes.

Subject-matter of the invention are also polypeptides with phosphomevalonate kinase activity which are encoded by an abovementioned DNA.

The skilled worker knows that the polypeptides of the present invention can be obtained by various routes, for example by chemical methods such as the solid-phase method. The use of recombinant methods is recommended for obtaining larger amounts of protein. Expression of a cloned phosphomevalonate kinase gene or fragments thereof can be effected in a series of suitable host cells with which the skilled worker is familiar. To this end, a phosphomevalonate kinase gene is introduced into a host cell with the aid of known methods.

The integration of the cloned phosphomevalonate kinase gene into the chromosome of the host cell is within the scope of the present invention. Preferably, the gene or fragments thereof are introduced into a plasmid and the coding regions of the phosphomevalonate kinase gene or fragments thereof are linked functionally with a constitutive or inducible promoter.

The basic steps for generating the recombinant phosphomevalonate kinase are:

1. Obtaining a natural, synthetic or semisynthetic DNA which encodes phosphomevalonate kinase.
2. Introduction of this DNA into an expression vector which is suitable for expressing phosphomevalonate kinase, either alone or as fusion protein.
3. Transformation of a suitable, preferably prokaryotic, host cell with this expression vector.
4. Growing this transformed host cell in a manner which is suitable for expressing phosphomevalonate kinase.
5. Cell harvest and purification of phosphomevalonate kinase by suitable known methods.

The coding region of phosphomevalonate kinase can be expressed in E. coli by the customary methods. Suitable expression systems for E. coli are commercially available, for example the expression vectors of the pET series, for example pET3a, pET23a, pET28a with His tag or pET32a with His tag for simple purification and thioredoxin fusion for increasing the solubility of the enzyme expressed, and pGEX with glutathione synthetase fusion, and the pSPORT vectors. The expression vectors are transformed into λ DE3 lysogenic E. coli strains, for example BL21(DE3), HMS 174(DE3) or AD494(DE3). After the growth of the cells under standard conditions which are familiar to the skilled worker, expression is induced by means of IPTG. After induction, the cells are incubated for 3 to 24 at temperatures from 18 to 37° C. The cells are disrupted by sonification in breaking buffer (10 to 200 mM sodium phosphate, 100 to 500 mM NaCl, pH 5 to 8). The protein expressed can be purified by chromatographic methods, in the case of protein expressed with His tag by chromatography on an Ni-NTA column.

Expression of the protein in commercially available yeast strains (for example *Pichia pastoris*) or in insect cell cultures (for example Sf9 cells) constitutes another advantageous approach.

Alternatively, the proteins may also be expressed in plants.

Subject-matter of the present invention are also methods for finding chemical compounds which bind to the polypeptides according to the invention and modify their properties. Owing to the many functions of the terpenoids which make necessary the formation of the precursor isopentyl diphosphate and thus the function of the phosphomevalonate kinase according to the invention, modulators which affect the activity of the enzyme constitute new growth-regulatory or herbicidally active compounds. Modulators may take the form of agonists or antagonists, or activators or inhibitors.

Subject-matter of the present invention is therefore in particular also the use of plant phosphomevalonate kinases as targets for herbicides and their use in methods for finding modulators of this polypeptide. In such methods, the phosphomevalonate kinases can be employed directly, in extracts or in purified form, or they can be formed indirectly via expression of the DNA encoding them.

Subject-matter of the present invention is therefore also the use of nucleic acids encoding plant PMVK, DNA constructs comprising them, host cells comprising them, or of antibodies binding to PMVK for finding PMVK modulators.

The term "agonist" as used in the present context refers to a molecule which accelerates or increases the activity of phosphomevalonate kinase.

The term "antagonist" as used in the present context refers to a molecule which slows down or prevents the activity of phosphomevalonate kinase.

The term "modulator" as used in the present context constitutes the generic term for agonist or antagonist. Modulators can be small organochemical molecules, peptides or antibodies which bind to the polypeptides according to the invention. Other modulators may be small organochemical molecules, peptides or antibodies which bind to a molecule which, in turn, binds to the polypeptides according to the invention, thus affecting their biological activity. Modulators may constitute natural substrates and ligands or their structural or functional mimetics. The term "modulator", however, does not encompass the natural substrates and ATP.

The modulators are preferably small organochemical compounds.

The binding of the modulators to the phosphomevalonate kinases according to the invention can alter the cellular processes in a manner which leads to the death of the plants treated therewith.

Subject-matter of the present invention are therefore also modulators, preferably inhibitors of the enzymatic activity of plant phosphomevalonate kinases, which were found with the aid of one of the processes described hereinbelow for identifying modulators of the phosphomevalonate kinase protein or a polypeptide which is homologous therewith.

Subject-matter of the invention is additionally the use of modulators of phosphomevalonate kinase as herbicides.

The present invention furthermore encompasses methods for finding chemical compounds which modify the expression of the polypeptides according to the invention. Such "expression modulators" too may constitute new growth-regulatory or herbicidal active compounds. Expression modulators can be small organochemical molecules, peptides or antibodies which bind to the regulatory regions of the nucleic acids encoding the polypeptides according to the invention. Furthermore, expression modulators can be small organochemical molecules, peptides or antibodies which bind to a molecule which, in turn, binds to regulatory regions of the nucleic acids encoding the polypeptides according to the invention, thus affecting their expression. Expression modulators may also be antisense molecules.

The present invention therefore also extends to the use of modulators of the polypeptides according to the invention or of expression modulators as plant growth regulators or herbicides.

Subject-matter of the present invention are also expression modulators of phosphomevalonate kinases which are formed with the aid of an above-described method of identifying expression modulators of the phosphomevalonate kinase protein or a polypeptide which is homologous thereto.

Subject-matter of the invention is also the use of expression modulators as herbicides.

Other methods according to the invention include high-throughput screening (HTS). Both host cells and cell-free preparations comprising the nucleic acids according to the invention and/or the polypeptides according to the invention may be used for this purpose.

In order to find modulators of the polypeptides according to the invention, a synthetic reaction mix (for example products of in vitro transcription) or a cellular component, such as a crude cell extract, or any other preparation comprising the polypeptide according to the invention can be incubated together with a labelled substrate or ligand of the polypeptides in the presence and absence of a candidate molecule, which may be an agonist or antagonist. The ability of the candidate molecule to increase or inhibit the activity of the polypeptide according to the invention can be seen from an increased or reduced binding of the labelled ligand or an increased or reduced conversion rate of the labelled substrate. Molecules which bind well and lead to an increased activity of the polypeptides according to the invention are agonists. Molecules which bind well but do not trigger the biological activity of the polypeptides according to the invention are probably good antagonists.

The detection of the biological activity of the polypeptides according to the invention can be improved by what is known as a reporter system. Reporter systems in this regard encompass, but are not limited to, colorimetrically labelled substrates which are converted into a product, or a reporter gene which responds to changes in the activity or the expression of the polypeptides according to the invention, or other known binding tests.

Modulators of the polypeptide according to the invention can also be found via enzymatic tests. The change in the enzyme activity by suitable modulators can either be measured directly or indirectly in a coupled enzyme test. The measurement can be carried out for example via the change in absorption owing to the decrease or increase of an optically active compound.

A further example of a method by means of which modulators of the polypeptides according to the invention can be found is a displacement test, in which the polypeptides according to the invention and a potential modulator are combined under conditions suitable for this test with a molecule which is known to bind to the polypeptides according to the invention, such as a natural substrate or ligand or a substrate or ligand mimetic. The polypeptides according to the invention themselves can be labelled, for example radiolabelled or colorimetrically labelled, so that the number of polypeptides which are bound to a ligand or which have undergone conversion can be determined accurately. In this manner, the efficacy of an agonist or antagonist can be assessed.

EXAMPLES

Example 1

Isolation of the Nucleic Acid Encoding *A. thaliana* PMVK

A 370 bp PMVK fragment was repeatedly isolated from leaf material of *Arabidopsis thaliana* cv. Columbia plants with the aid of the suppression subtractive hybridization method (Diatchenko et al., 1996).

Suppression subtractive hybridization constitutes a method of isolating differentially expressed genes. The two samples to be compared were on the one hand Arabidopsis plants which had been harvested 24 hours after treatment with a herbicide (chlorsulfuron, 10 g/ha) and, on the other hand, Arabidopsis plants which had been harvested 24 hours after a control treatment. The 370 bp PMVK fragment was isolated from the chlorsulfuron-treated plants in which PMVK transcription may have been induced by the treatment.

The fragment obtained was cloned into vector pTAdv (Clontech) and transformed into *E. coli* strain TOP10F'. The PMVK fragment was furthermore used as probe for virtual Northern (Clontech) blots and employed as probe for isolating the complete PMVK cDNA.

Isolation of the Complete PMVK cDNA Sequence

An Arabidopsis cDNA library by Life Technologies in the plasmid vector pSPORT was screened with the aid of Clontech's Cloncapture kit following the manufacturer's instructions. However, as opposed to the manufacturer's instructions, Biotin labelling of the PMVK fragment employed as probe was not carried out by means of PCR, but with the aid of Boehringer's Biotin High Prime kit.

The PMVK-enriched plasmid DNA was transformed into *E. coli* cells and plated out overnight. The resulting colonies were analysed by colony PCR with PMVK-gene-specific primers, and positive colonies were identified.

Cultures from the positive colonies were grown by methods known to the skilled worker, and the plasmid DNA was isolated and the DNA was subsequently sequenced.

Example 2

To verify differential PMVK expression in the response to chlorsulfuron, so-called virtual Northern blot analyses were carried out.

In a virtual Northern blot, cDNA is prepared from total RNA with Clontech's SMART method (see manufacturer's instructions) and amplified by PCR. A low enough number of PCR cycles is employed so that the amplification is still within the linear range of the PCR. In the present case, an optimum between 15 and 18 cycles emerged. The SMART cDNA is separated on an agarose gel by methods known to the skilled worker, transferred to a nylon membrane and hybridized with a DIG-labelled probe. This method permits study of the expression even of genes with a low expression level.

The result showed a low degree of induction of PMVK expression by chlorsulfuron.

Example 3

A potential assay system for identifying modulators of phosphomevalonate kinase is based on the ADP detection of the coupled pyruvate kinase/lactate dehydrogenase assay.

Phosphoenol pyruvate is converted to pyruvate by pyruvate kinase, and pyruvate is then subsequently converted to lactate by lactate dehydrogenase with consumption of NADH. The consumption of NADH can be monitored by the decreasing absorption at 340 nm.

In the reaction of PMVK, ADP is formed, which can be detected in the assays described. The effect of PMVK modulators on this reaction can thus also be determined with reference to an increase or decrease in the ADP content.

Figures and Sequence Listing

FIG. 1

References

Altschul, S. F., Madden, T. L., Schaffer, A. A., Zhang, J. Z.; Miller W. and Lipman, D. J. 1997. Gapped BLAST and PSI-BLAST generation of protein database search programs. Nucleic Acids Res. 25: 3389–3402.

Bevan, M. 1984. Binary Agrobacterium vectors for plant transformation. Nucleic Acids Res 12(22): 8711–8721.

Croteau, R., 1992. Clomazone Does Not Inhibit the Conversion of Isopentyl Pyrophosphate to Geranyl, Farnesyl, or Geranylgeranyl Pyrophosphate in Vitro. Plant Physiol. 98, 1515–1517

Diatchenko, L., Lau, Y. C., Campbell, A. P., Chenchik, A., Moqadam, F., Huang, B., Lukyanov, S., Lukyanov, K., Gurskaya, N., Sverdlov, E. D., Siebert, P. D. 1996. Suppression subtractive hybridization: A method for generating differentially regulated or tissue-specific cDNA probes and libraries. *Proc. Natl. Acad. Sci.* USA 93, 6025–6030

Heintze, A., Görlach, J., Schulze-Siebert, D., Schultz, G. 1990. Plastidic isoprenoid synthesis during chloroplast development. Change from metabolic autonomy to division-of-labor stage. Plant Physiol. 93, 1121–1127

Lottspeich, F., Zorbas H. (Eds.). 1998. Bioanalytik. Spektrum Akademischer Verlag, Heidelberg, Berlin.

Minet, M., Dufour, M.-E. and Lacroute, F. 1992. Complementation of *Saccharomyces cerevisiae* auxotrophic mutants by *Arabidopsis thaliana* cDNAs. Plant J. 2: 417–422.

Mumberg, D., Müller, R., Funk, M.,. 1995. Yeast vectors for the controlled expression of heterologous proteins in different genetic backgrounds. Gene 156, 119–122.

Norman, M. A., Liebi, R. A., Widholm, J. M., 1990. Site of Clomazone Action in Tolerant-Soybean and Susceptible-Cotton Photomixotrophic Cell Suspension Cultures. Plant Physiol. 94, 704–709

Weimar, M. R., Balke, N. E., Buhler, D. D., 1992. Herbicide Clomazone Does Not Inhibit In Vitro Geranylgeranyl Synthesis from Mevalonate. Plant Physiol. 98, 427–432

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method of identifying a herbicide comprising:

(a) contacting a host cell said host cell including a polypeptide, said polypeptide having the biological activity of a phosphomevelonate kinase and comprising an amino acid sequence having at least 80% identity with the sequence according to SEQ ID NO:2, with a chemical compound or mixture of chemical compounds under conditions which permit the interaction of the chemical compound or the mixture of chemical compounds with the polypeptide, (b) comparing the biological activity of the polypeptide in the presence of the chemical compound or the mixture of chemical compounds with the biological activity of the polypeptide in the absence of the chemical compound or the mixture of chemical compounds, and (C) determining the chemical compound which specifically modulates the biological activity of the polypeptide thereby identifying the herbicide.

2. The method of claim 1, wherein said polypeptide comprises the amino acid sequence of SEQ ID NO: 2.

3. A method of finding a herbicide comprising:

(a) contacting a polypeptide having the biological activity of a phosphomevalonate kinase and comprising an amino acid sequence having at least 80% identity with the sequence according to SEQ ID NO: 2, with a chemical compound or a mixture of chemical compounds under conditions which permit the interaction of the chemical compound or mixture of chemical compounds with the polypeptide;

(b) comparing the biological activity of the polypeptide in the presence of the chemical compound or the mixture of chemical compounds with the biological activity of the polypeptide in the absence of the chemical compound or the mixture of chemical compounds, and (c) determining the chemical compound which specifically modulates the biological activity of the polypeptide, thereby identifying the herbicide.

4. The method of claim 2, wherein said polypeptide comprises the amino acid sequence of SEQ ID NO: 2.

* * * * *

SEQUENCE LISTING

```
<160> NUMBER OF SEQ ID NOS: 5

<210> SEQ ID NO 1
<211> LENGTH: 2396
<212> TYPE: DNA
<213> ORGANISM: Arabidopsis thaliana
<220> FEATURE:
<221> NAME/KEY: CDS
<222> LOCATION: (685)..(2199)

<400> SEQUENCE: 1
gtcgacccac gcgtccgggc cgaccttctt cttcttcctt aagacaacac ataatgatag      60
aagcaaactg gggaagatga agatggagtg gtgaagaaca aaaccgtata accgttcggt     120
tcagaggtgc cgaaccgaac cgacccgtaa accgaaatcc tcaaaagaaa ttgccgatcg     180
gtttgctact gttcaaaacc tcggtgccga gaaccgaaac tgtcggtttt ttcggttcgg     240
gtttctcggt ttcttccgaa ctcccaggcc tagtttggtt ttattttttca cgagttttgc     300 ttctcttttc atcggcgacg acgacgtcga gtttctgtca aaacgttaac gatccgactc     360
gagcgtcgac agtaagagaa gaagacagcg attgtgtgta gatcgacggc gaacgtgtgt     420
cgatccgtct cgatcgacgg agaatacgtt tcgatccggt ttcgatccaa atcggagagt     480
ttgaggatct aaatcggaaa ttgcattaat actcatctcc aatctcttct gaagagtccg     540
aatccgatct accaccacta ctcgtaccgc cggtcattta ctgccgccga tttcaaatta     600
tccgatcatt tccggcgata tccaatcgca gactgaggtg aatctggggt tttgatcagc     660
gattatcttt gtcactcttt gaaa atg gct gtt gtt gct tct gct cct ggg        711
                            Met Ala Val Val Ala Ser Ala Pro Gly
                              1               5 aaa gtt ttg atg act gga ggc tac ctt gta ctc gag aag cca aat gca       759
Lys Val Leu Met Thr Gly Gly Tyr Leu Val Leu Glu Lys Pro Asn Ala
 10              15                  20                  25 ggg ctt gtg ttg agt aca aat gca cgg ttt tac gcg att gtg aag cca       807
Gly Leu Val Leu Ser Thr Asn Ala Arg Phe Tyr Ala Ile Val Lys Pro
                 30                  35                  40 atc aac gaa gaa gtc aag cct gaa agt tgg gca tgg aaa tgg aca gat       855
Ile Asn Glu Glu Val Lys Pro Glu Ser Trp Ala Trp Lys Trp Thr Asp
             45                  50                  55 gtc aaa tta aca tca cca cag ctc tcg aga gaa agc atg tat aaa ctg       903
Val Lys Leu Thr Ser Pro Gln Leu Ser Arg Glu Ser Met Tyr Lys Leu
         60                  65                  70 tca ctg aat cat ttg act ctt cag tct gtg tct gca agt gat tca aga       951
Ser Leu Asn His Leu Thr Leu Gln Ser Val Ser Ala Ser Asp Ser Arg
     75                  80                  85
```

|  |  |
|---|---|
| aac ccc ttt gta gag cat gcg ata cag tat gct ata gct gct gct cat<br>Asn Pro Phe Val Glu His Ala Ile Gln Tyr Ala Ile Ala Ala Ala His<br>90                       95                    100                   105 | 999 |
| ttg gca acc gag aag gac aaa gaa tca ttg cac aaa ctc tta ttg caa<br>Leu Ala Thr Glu Lys Asp Lys Glu Ser Leu His Lys Leu Leu Leu Gln<br>                  110                    115                   120 | 1047 |
| ggt ctt gat ata aca ata tta ggc tcc aat gac ttt tac tca tat cgg<br>Gly Leu Asp Ile Thr Ile Leu Gly Ser Asn Asp Phe Tyr Ser Tyr Arg<br>              125                    130                   135 | 1095 |
| aac cag ata gaa tcg gct ggg ctt cca ttg aca cca gaa tcg ctg ggt<br>Asn Gln Ile Glu Ser Ala Gly Leu Pro Leu Thr Pro Glu Ser Leu Gly<br>        140                    145                   150 | 1143 |
| acc ctt gca ccg ttt gca tca atc aca ttc aat gct gcg gag tca aat<br>Thr Leu Ala Pro Phe Ala Ser Ile Thr Phe Asn Ala Ala Glu Ser Asn<br>155                      160                    165 | 1191 |
| ggt gct aat tcc aag cct gaa gta gca aaa act ggc tta ggt tct tct<br>Gly Ala Asn Ser Lys Pro Glu Val Ala Lys Thr Gly Leu Gly Ser Ser<br>170                      175                    180                   185 | 1239 |
| gca gca atg aca aca gct gtg gtt gca gct ctg tta cat tat ctt gga<br>Ala Ala Met Thr Thr Ala Val Val Ala Ala Leu Leu His Tyr Leu Gly<br>                  190                    195                   200 | 1287 |
| gtg gtt gac cta tct gat cca tgt aaa gaa gga aag ttt ggc tgt tct<br>Val Val Asp Leu Ser Asp Pro Cys Lys Glu Gly Lys Phe Gly Cys Ser<br>              205                    210                   215 | 1335 |
| gat cta gat gtt atc cat atg ata gca caa acg tct cat tgt ctt gca<br>Asp Leu Asp Val Ile His Met Ile Ala Gln Thr Ser His Cys Leu Ala<br>        220                    225                   230 | 1383 |
| caa ggg aag gtc gga agt ggg ttt gat gtc agc tgt gct gtc tat gga<br>Gln Gly Lys Val Gly Ser Gly Phe Asp Val Ser Cys Ala Val Tyr Gly<br>              235                    240                   245 | 1431 |
| agt cag cgt tat gtt cgc ttc tct cca gaa gtc ttg tca ttt gct cag<br>Ser Gln Arg Tyr Val Arg Phe Ser Pro Glu Val Leu Ser Phe Ala Gln<br>250                      255                    260                   265 | 1479 |
| gtt gca gta aca ggt ctg cca tta aat gaa gtt att ggt aca att ttg<br>Val Ala Val Thr Gly Leu Pro Leu Asn Glu Val Ile Gly Thr Ile Leu<br>                  270                    275                   280 | 1527 |
| aag gga aaa tgg gac aat aag aga act gag ttc tct tta cca cca ctg<br>Lys Gly Lys Trp Asp Asn Lys Arg Thr Glu Phe Ser Leu Pro Pro Leu<br>              285                    290                   295 | 1575 |
| atg aat ctt ttc ctt gga gaa cct gga agt ggt gga tcc tcc aca cca<br>Met Asn Leu Phe Leu Gly Glu Pro Gly Ser Gly Gly Ser Ser Thr Pro<br>        300                    305                   310 | 1623 |
| tca atg gta ggt gca gta aag aag tgg caa atg tct gat cca gag aag<br>Ser Met Val Gly Ala Val Lys Lys Trp Gln Met Ser Asp Pro Glu Lys<br>315                      320                    325 | 1671 |
| gca cga gaa aac tgg cag aat ttg tca gat gca aat tta gaa ctg gaa<br>Ala Arg Glu Asn Trp Gln Asn Leu Ser Asp Ala Asn Leu Glu Leu Glu<br>330                      335                    340                   345 | 1719 |
| act aag cta aac gat ctg agc aaa tta gct aaa gac cac tgg gat gtt<br>Thr Lys Leu Asn Asp Leu Ser Lys Leu Ala Lys Asp His Trp Asp Val<br>                  350                    355                   360 | 1767 |
| tat cta cga gtc att aag tct tgt agt gtg ctt act tct gaa aag tgg<br>Tyr Leu Arg Val Ile Lys Ser Cys Ser Val Leu Thr Ser Glu Lys Trp<br>              365                    370                   375 | 1815 |
| gtg tta cat gct act gaa cca atc aac gaa gcc att att aaa gaa ctc<br>Val Leu His Ala Thr Glu Pro Ile Asn Glu Ala Ile Ile Lys Glu Leu<br>        380                    385                   390 | 1863 |
| tta gag gca aga gaa gct atg ttg agg atc aga att ctt atg cgt cag<br>Leu Glu Ala Arg Glu Ala Met Leu Arg Ile Arg Ile Leu Met Arg Gln<br>395                      400                    405 | 1911 |

-continued

| | |
|---|---|
| atg ggt gag gcg gct agc gtt ccg ata gag cct gaa tct caa act caa<br>Met Gly Glu Ala Ala Ser Val Pro Ile Glu Pro Glu Ser Gln Thr Gln<br>410      415      420      425 | 1959 |
| ctt ttg gat tct aca atg agt gct gaa gga gtt cta ctt gct ggt gtt<br>Leu Leu Asp Ser Thr Met Ser Ala Glu Gly Val Leu Leu Ala Gly Val<br>      430      435      440 | 2007 |
| cct gga gct ggt gga ttt gat gcc ata ttt gca atc act tta ggg gat<br>Pro Gly Ala Gly Gly Phe Asp Ala Ile Phe Ala Ile Thr Leu Gly Asp<br>445      450      455 | 2055 |
| tcc ggc acc aaa ctg acc cag gca tgg agt tcg cac aat gtt ttg gcc<br>Ser Gly Thr Lys Leu Thr Gln Ala Trp Ser Ser His Asn Val Leu Ala<br>460      465      470 | 2103 |
| ttg ttg gtg aga gaa gat cca cat ggc gtt tgc cta gaa agt ggt gat<br>Leu Leu Val Arg Glu Asp Pro His Gly Val Cys Leu Glu Ser Gly Asp<br>475      480      485 | 2151 |
| cca cga acc aca tgt att act tca ggc gtt tca tca att cac ctt gag<br>Pro Arg Thr Thr Cys Ile Thr Ser Gly Val Ser Ser Ile His Leu Glu<br>490      495      500      505 | 2199 |
| taaacaacat tgtttcagtg tccaattatt aggtgcgtca ccaagttcgg ttgagtatac | 2259 |
| tgttttgcat atagacttgg gtgctaaatt tcttggtgta agcattttta tacccattgt | 2319 |
| aaggtcttta actcttggaa aacttgcggg aaaataaaat aaagttgatt tcaaatcttc | 2379 |
| tcaaaaaaaa aaaaaaa | 2396 |

<210> SEQ ID NO 2
<211> LENGTH: 505
<212> TYPE: PRT
<213> ORGANISM: Arabidopsis thaliana

<400> SEQUENCE: 2

Met Ala Val Val Ala Ser Ala Pro Gly Lys Val Leu Met Thr Gly Gly
1      5      10      15

Tyr Leu Val Leu Glu Lys Pro Asn Ala Gly Leu Val Leu Ser Thr Asn
      20      25      30

Ala Arg Phe Tyr Ala Ile Val Lys Pro Ile Asn Glu Glu Val Lys Pro
    35      40      45

Glu Ser Trp Ala Trp Lys Trp Thr Asp Val Lys Leu Thr Ser Pro Gln
  50      55      60

Leu Ser Arg Glu Ser Met Tyr Lys Leu Ser Leu Asn His Leu Thr Leu
65      70      75      80

Gln Ser Val Ser Ala Ser Asp Ser Arg Asn Pro Phe Val Glu His Ala
      85      90      95

Ile Gln Tyr Ala Ile Ala Ala His Leu Ala Thr Glu Lys Asp Lys
    100      105      110

Glu Ser Leu His Lys Leu Leu Leu Gln Gly Leu Asp Ile Thr Ile Leu
  115      120      125

Gly Ser Asn Asp Phe Tyr Ser Tyr Arg Asn Gln Ile Glu Ser Ala Gly
130      135      140

Leu Pro Leu Thr Pro Glu Ser Leu Gly Thr Leu Ala Pro Phe Ala Ser
145      150      155      160

Ile Thr Phe Asn Ala Ala Glu Ser Asn Gly Ala Asn Ser Lys Pro Glu
      165      170      175

Val Ala Lys Thr Gly Leu Gly Ser Ser Ala Ala Met Thr Thr Ala Val
    180      185      190

Val Ala Ala Leu Leu His Tyr Leu Gly Val Val Asp Leu Ser Asp Pro
  195      200      205

```
Cys Lys Glu Gly Lys Phe Gly Cys Ser Asp Leu Asp Val Ile His Met
        210                 215                 220

Ile Ala Gln Thr Ser His Cys Leu Ala Gln Gly Lys Val Gly Ser Gly
225                 230                 235                 240

Phe Asp Val Ser Cys Ala Val Tyr Gly Ser Gln Arg Tyr Val Arg Phe
                245                 250                 255

Ser Pro Glu Val Leu Ser Phe Ala Gln Val Ala Val Thr Gly Leu Pro
                260                 265                 270

Leu Asn Glu Val Ile Gly Thr Ile Leu Lys Gly Lys Trp Asp Asn Lys
            275                 280                 285

Arg Thr Glu Phe Ser Leu Pro Pro Leu Met Asn Leu Phe Leu Gly Glu
        290                 295                 300

Pro Gly Ser Gly Gly Ser Ser Thr Pro Ser Met Val Gly Ala Val Lys
305                 310                 315                 320

Lys Trp Gln Met Ser Asp Pro Glu Lys Ala Arg Glu Asn Trp Gln Asn
                325                 330                 335

Leu Ser Asp Ala Asn Leu Glu Leu Glu Thr Lys Leu Asn Asp Leu Ser
            340                 345                 350

Lys Leu Ala Lys Asp His Trp Asp Val Tyr Leu Arg Val Ile Lys Ser
        355                 360                 365

Cys Ser Val Leu Thr Ser Glu Lys Trp Val Leu His Ala Thr Glu Pro
370                 375                 380

Ile Asn Glu Ala Ile Ile Lys Glu Leu Leu Glu Ala Arg Glu Ala Met
385                 390                 395                 400

Leu Arg Ile Arg Ile Leu Met Arg Gln Met Gly Glu Ala Ala Ser Val
                405                 410                 415

Pro Ile Glu Pro Glu Ser Gln Thr Gln Leu Leu Asp Ser Thr Met Ser
            420                 425                 430

Ala Glu Gly Val Leu Leu Ala Gly Val Pro Gly Ala Gly Gly Phe Asp
        435                 440                 445

Ala Ile Phe Ala Ile Thr Leu Gly Asp Ser Gly Thr Lys Leu Thr Gln
450                 455                 460

Ala Trp Ser Ser His Asn Val Leu Ala Leu Leu Val Arg Glu Asp Pro
465                 470                 475                 480

His Gly Val Cys Leu Glu Ser Gly Asp Pro Arg Thr Thr Cys Ile Thr
                485                 490                 495

Ser Gly Val Ser Ser Ile His Leu Glu
            500                 505

<210> SEQ ID NO 3
<211> LENGTH: 611
<212> TYPE: DNA
<213> ORGANISM: Medicago truncatula

<400> SEQUENCE: 3
ctgttatctg agttgaagaa atatcacaat atcaatggcc gtggtggttg cttctgctcc      60
tgggaaggtg ttaatgaccg gtggctacct agttttagag agacctaatg ctggacttgt     120
tcttagtact aatgctcgtt tttatgctat tgtcaaacca atctatcctc aaactaaacc     180
tgattcttgg gcttgggctt ggtcagatgt cagattaaca tctcctcaac tctccagaga     240
agccttctat aaattagcac tcaaaaatct taccatccaa actgtttcct caagtgaaac     300
aaggaaccct tttgtggaat atgctgtgca atactccgtg gctgccgcct atgcaacagc     360
tgaccagaat aaaaaggact tgttgcacaa actactttg caaggtcttg acattacaat      420
```

```
tttgggttcc aatgattttt attcttatag gaatgagatt gagagacacg gactcccttt       480
gacatcagaa tcattggcca cccttccgcc ttttgcctcc atttctttca atactgatga       540
tgctaatgga aggaattgta agcctgaaat tgccaaaact ggtttgggct catctgcagc       600
aatgacaacc g                                                            611

<210> SEQ ID NO 4
<211> LENGTH: 728
<212> TYPE: DNA
<213> ORGANISM: Gossypium hirsutum
<220> FEATURE:
<221> NAME/KEY: unsure
<222> LOCATION: 715
<223> OTHER INFORMATION: n can be any nucleotide

<400> SEQUENCE: 4 cgttttacg ctattgttaa gccaattcat gaagctatca agcctgaaag ctgggcatgg         60
tcttggaccg atgtcaagct aacatctcct cagctttcca gagaaagcat gtataaattg      120
tctcggaaac atttaacact tcagtgtgta tcttcaagtg aatcaaggaa ccctttgta       180 gaaaatgcta ttcaatatac tatagcagct gcacatgcaa catttgacaa gaataagaaa      240
gaggcattag ataaactact cttacaaggt cttgatatta cgatcttagg ttgcaatgac      300
ttttactcat acaggaatca gatagaagca cttggtcttc cgttgacacc tgaagcattg      360
gctactctac caccgtttac atcaattaca ttcaattctg aggaatcaaa tggagcaaat      420
tgcaaacctg aagttgcaaa aactggattg ggttcatctg cagcaatgac aactgctgta      480
gttgctgctt tacttcatta tcttggtgtt gttaaccttt ccacctcttc tgcagatcaa      540
caccaagaaa ataagaattc cacagatctc gatattgtgc atatgatagc tcaaagtgcc      600
cactgtattg cccaaggtaa agttggcagt ggctttgatg tcagttctgc tgtctatggg      660
agtcagcgtt atgttcgttt ttcaccaaaa gtgctttctg ctgctcaggc tgcantgaaa      720
gggatgcc                                                              728

<210> SEQ ID NO 5
<211> LENGTH: 571
<212> TYPE: DNA
<213> ORGANISM: Pinus radiata

<400> SEQUENCE: 5
cacaggcgaa accctctcct gctgctcacg gttgataaac cctcaatatt tgcggtaggg        60
ctccagattt actgcaatct gccagtaaga gtccgttgtg gcggaagaga gctgccgaga      120
gctgccgagc tggagagcac cattcgcacc atatagagaa gggggttgat agattcctgg      180
tcaaggaaaa ctgacaataa ggtgaaaaaa acaataatta ccttcagatt atctgatcat      240
cacatggctg tagttgtgtc agctcctggt aaggttttaa taacaggagc ttatctaatt      300
cttgagaagc caaatccagg acttgtgctt accaccacag ctcgcttcta cgccattgtg      360
aagccactgc ggactagcac agattccagt agttgggcat ggctatggac agatgtgaaa      420
ttaacatcgc ctcagcttgc aaaggaggcc atctacaagc tatctctgaa gactcttagc      480
ctgcaaaatg ttgcttcttc aagtagcaat ggtaatcctt ttgtggaaca agcagtgcaa      540
tttgctgttg cagctgcaaa agaagccttt g                                    571
```